(12) United States Patent
Andreev et al.

(10) Patent No.: US 9,897,531 B2
(45) Date of Patent: Feb. 20, 2018

(54) FLOW CYTOMETRY SAMPLE SEPARATION METHODS AND APPARATUS

(71) Applicant: Intellicyt, Albuquerque, NM (US)

(72) Inventors: Constantine I. Andreev, Albuquerque, NM (US); Matthew Hess, Albuquerque, NM (US); Joe Zock, Rio Rancho, NM (US)

(73) Assignee: Intellicyt, Albuquerque, NM (US)

( * ) Notice: Subject to any disclaimer, the term of this patent is extended or adjusted under 35 U.S.C. 154(b) by 16 days.

(21) Appl. No.: 14/729,838

(22) Filed: Jun. 3, 2015

(65) Prior Publication Data

US 2015/0346075 A1 Dec. 3, 2015

Related U.S. Application Data

(60) Provisional application No. 62/007,173, filed on Jun. 3, 2014.

(51) Int. Cl.
*G01N 15/14* (2006.01)

(52) U.S. Cl.
CPC ..... *G01N 15/1404* (2013.01); *G01N 15/1425* (2013.01); *G01N 2015/1415* (2013.01)

(58) Field of Classification Search
CPC ........... G01N 15/1404; G01N 15/1429; G01N 15/1415

See application file for complete search history.

(56) References Cited

U.S. PATENT DOCUMENTS

| | | | |
|---|---|---|---|
| 5,798,222 A | * | 8/1998 | Goix .............. C12Q 1/04 422/82.01 |
| 6,878,556 B2 | | 4/2005 | Sklar et al. |
| 6,890,487 B1 | | 5/2005 | Sklar et al. |
| 7,368,084 B2 | | 5/2008 | Sklar et al. |
| 7,842,244 B2 | | 11/2010 | Sklar et al. |
| 8,021,872 B2 | | 9/2011 | Sklar et al. |
| 8,268,571 B2 | | 9/2012 | Sklar et al. |
| 8,329,437 B1 | * | 12/2012 | Ayliffe .............. G01N 15/1056 422/68.1 |
| 8,823,943 B2 | | 9/2014 | Trinkle et al. |
| D722,515 S | | 2/2015 | Zock |

(Continued)

FOREIGN PATENT DOCUMENTS

| WO | 2010/005617 A3 | 1/2010 |
|---|---|---|
| WO | 2010/135627 A1 | 11/2010 |

*Primary Examiner* — Sang Nguyen
(74) *Attorney, Agent, or Firm* — McDonnell Boehnen Hulbert & Berghoff LLP (57) ABSTRACT

A method for identifying sample boundaries of a plurality of samples is provided. The method includes moving a plurality of samples comprising particles into a fluid flow stream using a sampling probe and introducing marker beads into the fluid flow stream between adjacent samples in the plurality of samples via the sampling probe to produce a marker bead-separated plurality of samples in the fluid flow stream. Marker beads may be introduced into the fluid flow stream by introducing the marker beads from a chamber surrounding at least a portion of the sampling probe, or by introducing the marker beads from a cartridge having a pierceable membrane underlying at least one chamber, the at least one chamber containing marker beads. Sampling systems and apparatuses are also provided.

20 Claims, 14 Drawing Sheets

(56) References Cited

U.S. PATENT DOCUMENTS

| | | |
|---|---|---|
| 9,012,235 B2 | 4/2015 | Trinkle et al. |
| 2003/0040105 A1* | 2/2003 | Sklar ................... B01F 13/0071 435/287.2 |
| 2003/0142291 A1* | 7/2003 | Padmanabhan ........ A61B 5/417 356/39 |
| 2008/0092655 A1* | 4/2008 | Takiguchi ............ G01N 29/036 73/584 |
| 2008/0152542 A1* | 6/2008 | Ball ................... G01N 15/1404 422/82.05 |
| 2008/0176253 A1* | 7/2008 | Christodoulides ... G01N 33/543 435/7.21 |
| 2009/0031814 A1* | 2/2009 | Takiguchi .......... G01N 15/1031 73/658 |
| 2010/0032584 A1* | 2/2010 | Dayong ................ G01N 15/14 250/459.1 |
| 2010/0197512 A1 | 8/2010 | Trinkle et al. |
| 2012/0006158 A1 | 1/2012 | Drnevich et al. |
| 2012/0061584 A1* | 3/2012 | Trinkle ............. G01N 15/0211 250/428 |
| 2012/0065047 A1* | 3/2012 | Chapman ............. B01L 3/5021 494/16 |
| 2012/0135405 A1* | 5/2012 | Toumbas ............. G01N 21/532 435/6.11 |
| 2012/0309635 A1 | 12/2012 | Trinkle et al. |
| 2014/0087389 A1* | 3/2014 | Heller ................ G01N 21/6486 435/6.15 |

\* cited by examiner

FLOW CYTOMETRY SAMPLE SEPARATION METHODS AND APPARATUS

CROSS-REFERENCE TO RELATED APPLICATIONS

This application claims priority to U.S. Provisional Application No. 62/007,173 filed Jun. 3, 2014, which is hereby incorporated by reference in its entirety.

BACKGROUND

Analyzing data from a high throughput flow cytometry system benefits from proper identification of each well sample as a distinct unit. In some flow cytometry detection systems, samples are identified by inserting a volume of marker bead suspension between consecutive samples. However, throughput in such systems is often decreased where a sampler arm has to travel to a marker bead reservoir after sampling each well. Additionally, the marker beads suspended in the fluid settle often out of the solution over time and the fluid must be periodically agitated to re-suspend the marker beads in order to maintain proper sample identification with the marker beads.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively.

The description of embodiments of the disclosure/examples is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize All embodiments of any aspect of the invention can be used in combination, unless the context clearly dictates otherwise.

SUMMARY

Methods and apparatuses for identifying sample boundaries of a plurality of samples are disclosed herein.

Some embodiments of the present disclosure provide a method for identifying sample boundaries of a plurality of samples, comprising: (a) moving a plurality of samples comprising particles into a fluid flow stream using a sampling probe; and (b) introducing marker beads into the fluid flow stream between adjacent samples in the plurality of samples via the sampling probe to produce a marker bead-separated plurality of samples in the fluid flow stream, wherein the marker beads are introduced by a method selected from the group consisting of: (i) introducing the marker beads from a chamber surrounding at least a portion of the sampling probe; and (ii) introducing the marker beads from a cartridge having a pierceable membrane underlying at least one chamber, the at least one chamber containing marker beads.

Further embodiments of the present disclosure provide a sampling apparatus, comprising: (1) a sampling probe having a sampling tip at a first end and a flow-stream outlet at a second end; (2) a chamber surrounding at least a portion of the sampling probe; and (3) a reservoir in fluid communication with the chamber and the sampling probe, wherein the chamber is movable with respect to the sampling probe between a retracted position and an extended position, wherein the sampling tip of the sampling probe is contained in the chamber in the extended position and the sampling tip of the sampling probe extends outside of the chamber in the retracted position.

Further embodiments of the present disclosure provide a sampling apparatus, comprising: (1) a sampling probe having a sampling tip at a first end and a flow-stream outlet at a second end; (2) a collar, wherein the sampling probe is coaxially aligned with and disposed at least partially within the collar; (3) a septum disposed at a distal end of the collar, an opening of the septum arranged co-linearly with the sampling probe; and (3) a reservoir in fluid communication with the collar and the sampling probe; wherein the sampling probe is movable with respect to the collar between a retracted position and an extended position, wherein sampling tip of the sampling probe is disposed within the collar in the in the retracted position and the sampling tip of the sampling probe extends through the opening in the septum in the extended position.

Still further embodiments of the present disclosure provide an apparatus comprising: a cartridge having at least one pierceable membrane underlying at least one chamber; wherein the cartridge is disposed over a sample plate and wherein the at least one chamber is configured to align with at least one sample well of the sample plate.

DETAILED DESCRIPTION

Methods and systems for acquiring between-well marker beads used to identify well-sample boundaries are described herein. In some examples, a solution of marker beads is physically positioned in such a way that the sample probe passes through a marker bead solution before and after the probe enters a test sample well. Since the system pump is continuously actively drawing pressure through the probe and attached length of tubing, a series of aliquots travel through the tubing which enables analysis software to identify the boundaries of those aliquots that were taken from sample wells.

A. Example Devices

Figure 1:
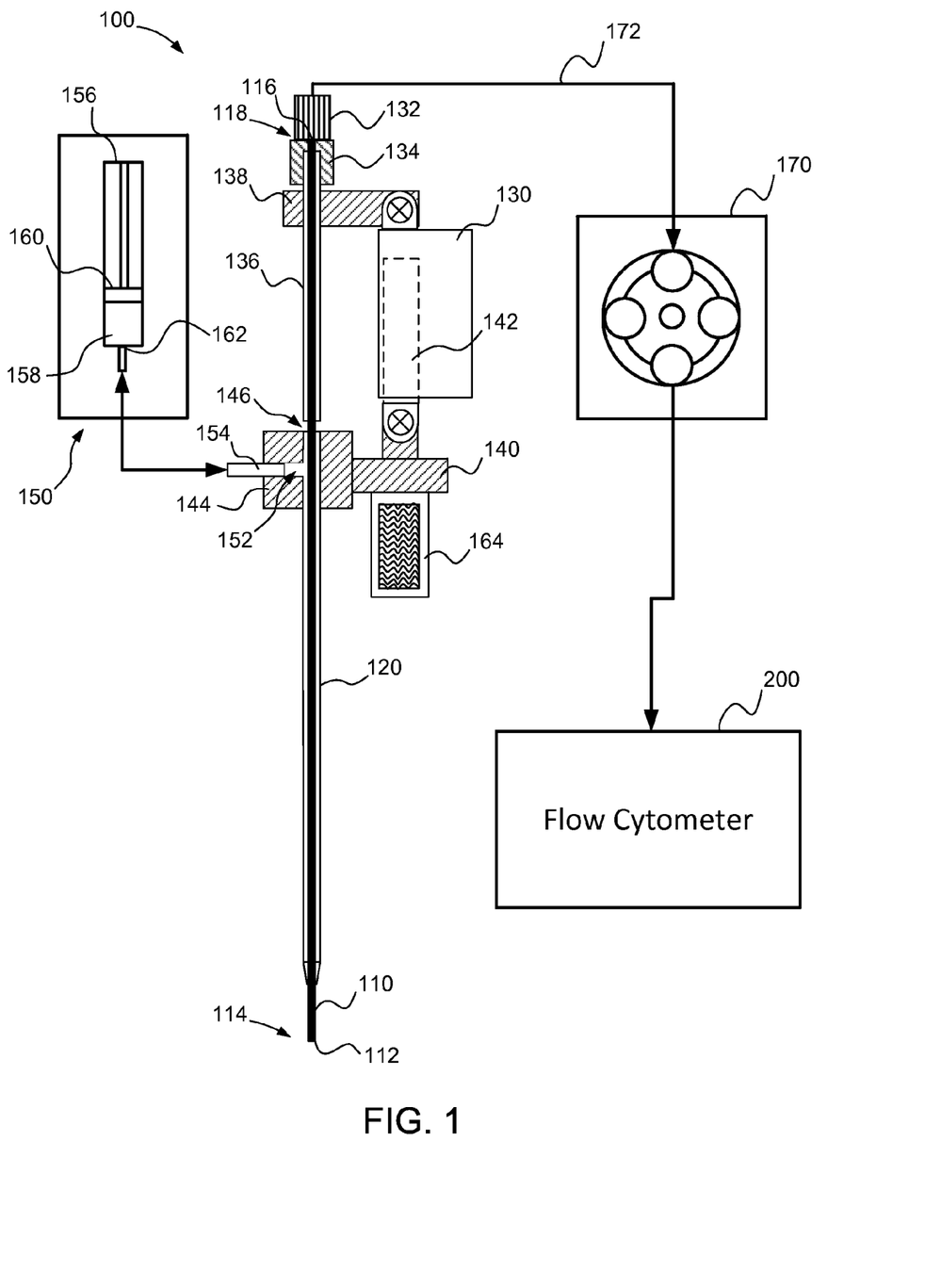
FIG. 1 illustrates an example sampling apparatus.
Figure 2A:
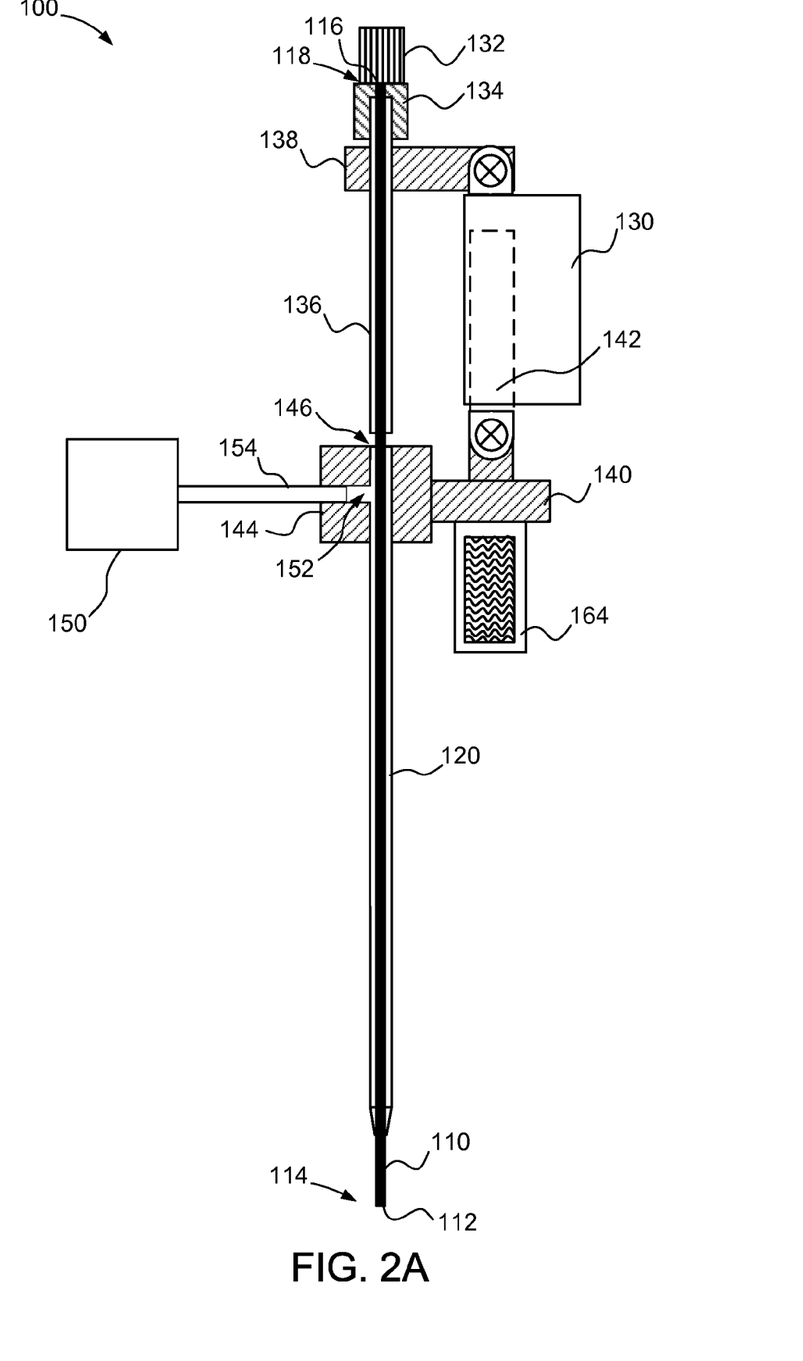
FIG. 2A illustrates the example sampling apparatus of FIG. 1, where the chamber is in a retracted state.
Figure 2B:
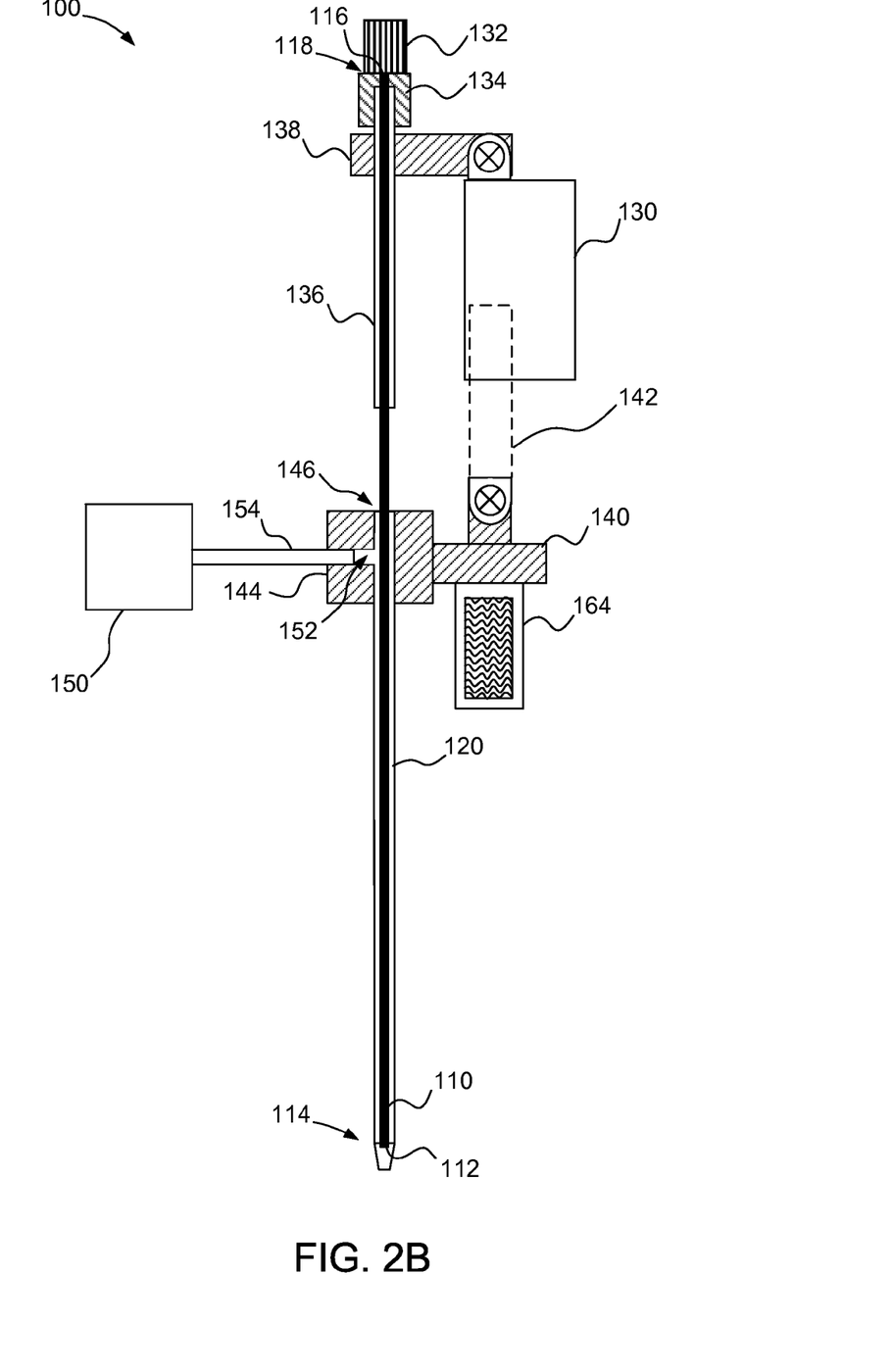
FIG. 2B illustrates the example sampling apparatus of FIG. 1, where the chamber is in an extended state.

FIGS. 1, 2A and 2B illustrate an example sampling apparatus 100 for use with a flow cytometer 200 in which well identification marker beads are supplied from a jacketed chamber surrounding the probe. This example apparatus 100 provides for the "in-line" use of marker beads, which may eliminate the need for the probe to travel to an off-plate marker bead supply cartridge, and thus reducing plate sampling times.

The sampling apparatus 100 includes a sampling probe 110, a chamber 120 surrounding at least a portion of the sampling probe 110, and a reservoir in fluid communication with the chamber 120 and the sampling probe 110. A marker bead solution is contained within the reservoir 150 and the chamber 120. The sampling probe 110 and the chamber 120 are held together by fluid tension created by the marker-bead solution contained therebetween. The sampling probe 110 includes a sampling tip 112 at a first end 114 and a flow-stream outlet 116 at a second end 118. As shown in FIGS. 2A and 2B, the chamber 120 is movable with respect to the sampling probe 110 between a retracted position (FIG. 2A) and an extended position (FIG. 2B), wherein the sampling tip 112 of the sampling probe 110 is contained in the chamber 120 in the extended position and the sampling tip 112 of the sampling probe 110 extends outside of the chamber 120, through an opening 122 at a distal end 12, in the retracted position.

The chamber 120 can be raised and lowered with respect to the sampling probe 120 by a linear actuator 130. The second end 118 of the sampling probe 110 connects to a nut 132 which is poisoned proximal to a guide nut 134, which connects to a probe guide 136 and through which the sampling probe 110 passes. The linear actuator 140 is coupled to the probe guide 136 via an upper bracket 138. A lower bracket 140 couples the driver 142 of the actuator 130 to the chamber 120 via a manifold 144. Fluid is retained within the chamber 120 by an interprobe seal 146 between an upper end of the chamber 120 near the manifold 144 and the sampling probe 110. The marker bead solution enters the chamber 120 via an inlet 152 in the manifold 144. Tubing 154 connects the reservoir 150 with the inlet 152.

In the embodiment shown in FIG. 1, the reservoir 150 is provided as a syringe pump 156 having a cavity 158 and a piston 160 displaceable within the cavity. The syringe outlet 162, defined in the cavity 158, is in fluid communication with the chamber 120, for example, by tubing 154. The syringe pump 156 introduces additional marker bead solution into the chamber 120 to replace the fluid drawn in to the sampling probe 110. A vibration motor 164, the utility of which will be described further below, may be connected to the lower bracket 140.

Figure 3A:
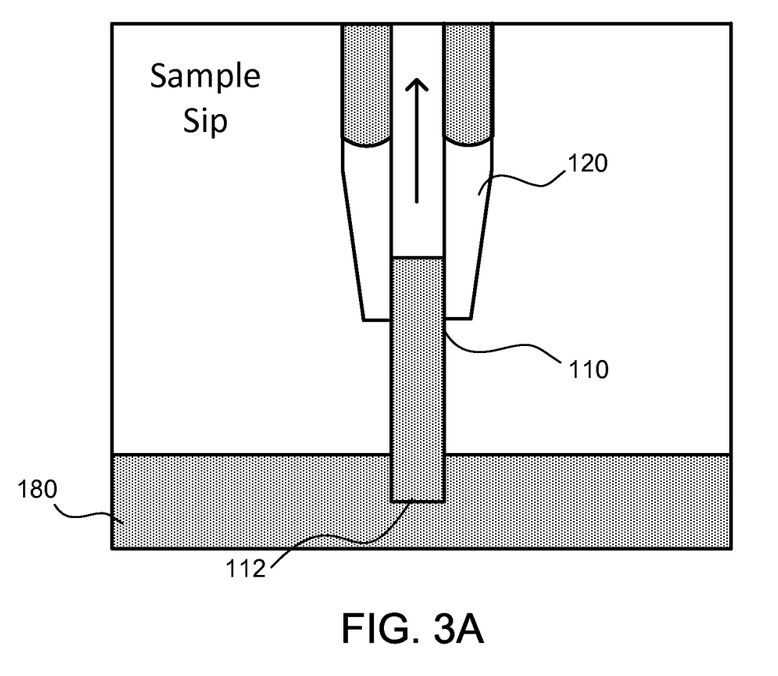
FIG. 3A is a view of a portion of the example sampling apparatus of FIG. 1.
Figure 3B:
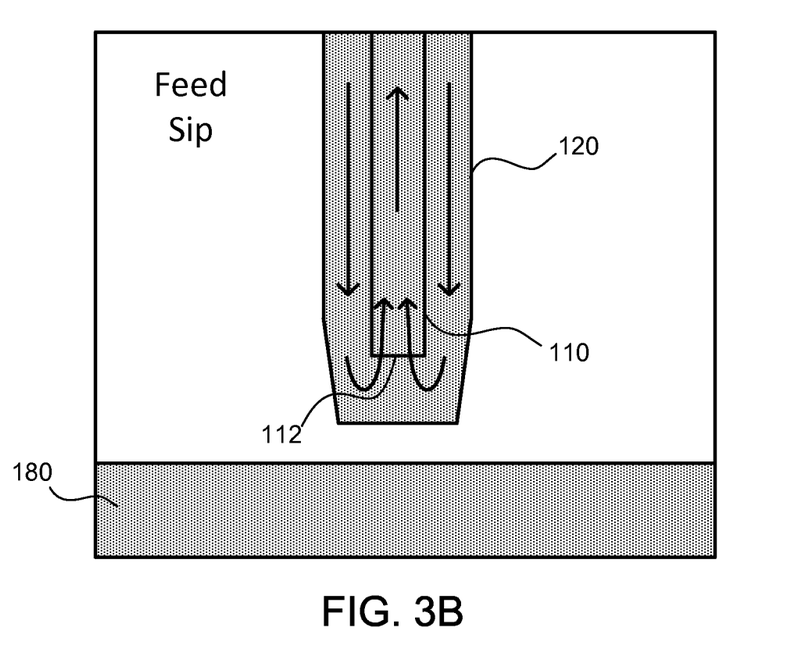
FIG. 3B is a view of a portion of the example sampling apparatus of FIG. 1.

A peristaltic pump 170, in fluid communication with the flow-stream outlet 116 of the sampling probe, draws fluid into the flow cytometer stream 172 via the sampling tip 112 of the sampling probe 110. The peristaltic pump 170 is also in fluid communication with the flow cytometer 200. In the extended position (FIG. 2B), the sampling probe 110 draws marker-bead solution into the flow cytometer stream 172 from the chamber 120. Turning to FIG. 3A, when the chamber 120 is raised, the exposed tip 112 of the sampling probe 110 can be submersed into a sample well 180 to draw a sample. As shown in FIG. 3B, after a sample is drawn into the flow cytometer stream 172, the sampling probe 110 is raised from the well and the chamber can be lowered by the linear actuator 130 to immerse the sample probe tip 112 into the chamber, from which it will draw marker bead solution. This mechanism allows the sampling probe 110 to take alternating sips from sample wells 180 and chamber 120.

Figure 3C:
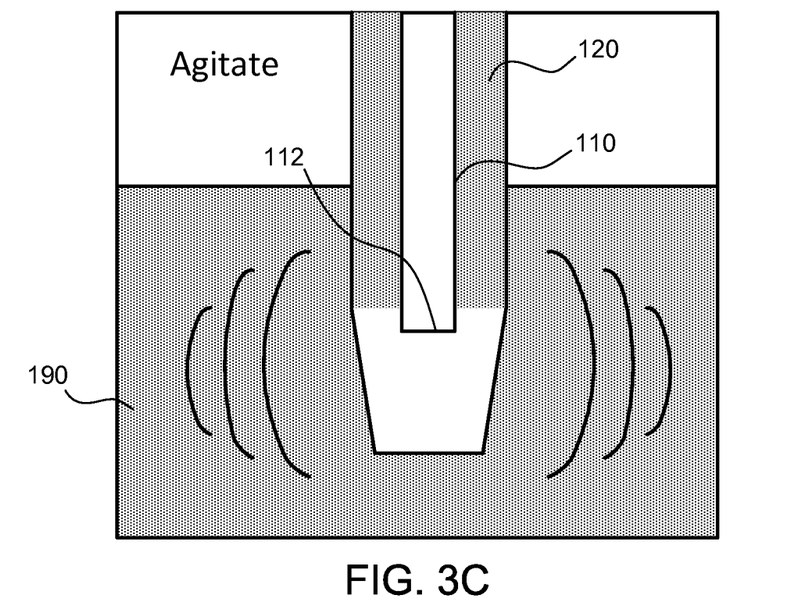
FIG. 3C is a view of a portion of the example sampling apparatus of FIG. 1.
Figure 3D:
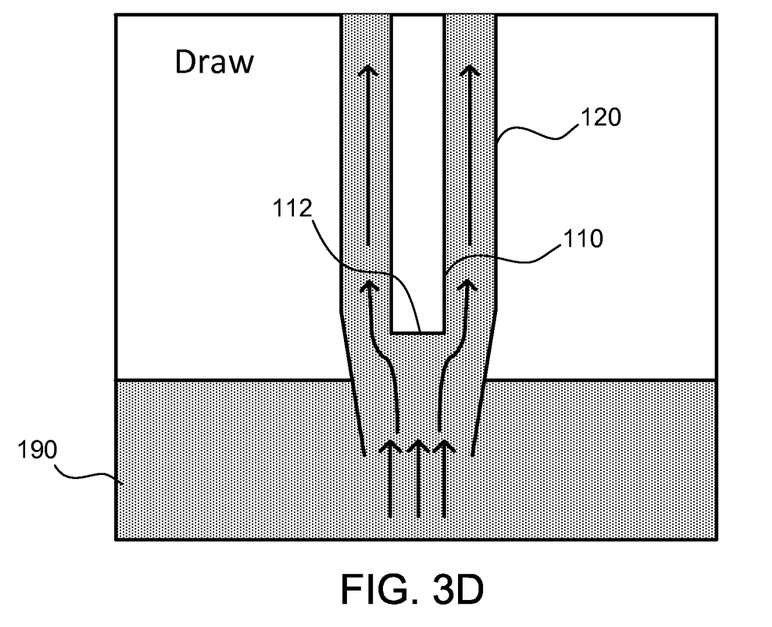
FIG. 3D is a view of a portion of the example sampling apparatus of FIG. 1.
Figure 3E:
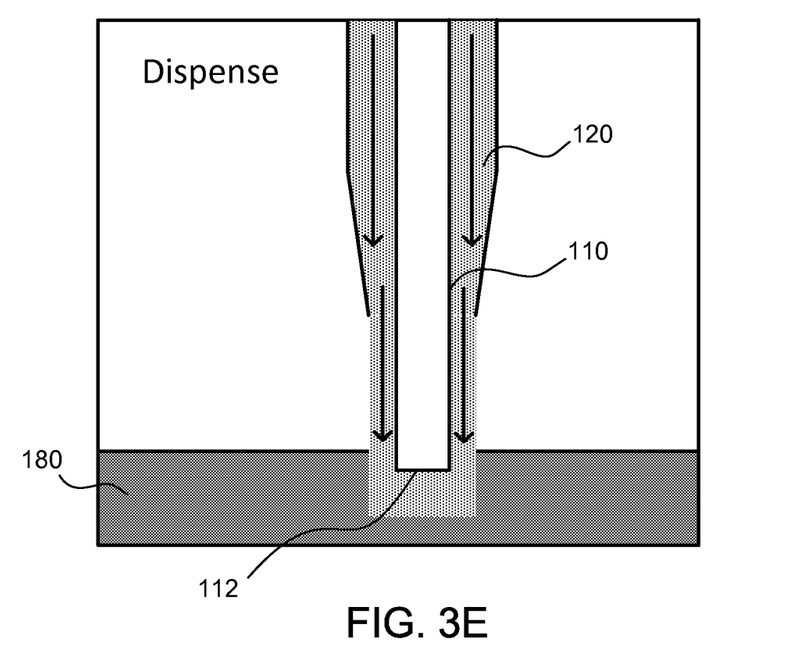
FIG. 3E is a view of a portion of the example sampling apparatus of FIG. 1.

Turning to FIG. 3C, the syringe pump 156 can be filled and refilled by submersing chamber 120 into a reservoir 190 containing, for example, a marker-bead solution and drawing the fluid into the chamber 120. The chamber 120 can be submersed in to the fluid reservoir 190 and vibrated, with the vibration motor 164, to agitate the fluid, as shown in FIG. 2D. In addition, with the peristaltic pump 170 turned off, the system 100 may also be used to dispense the fluid contained in the chamber 120 into a sample well 180.

Figure 4:
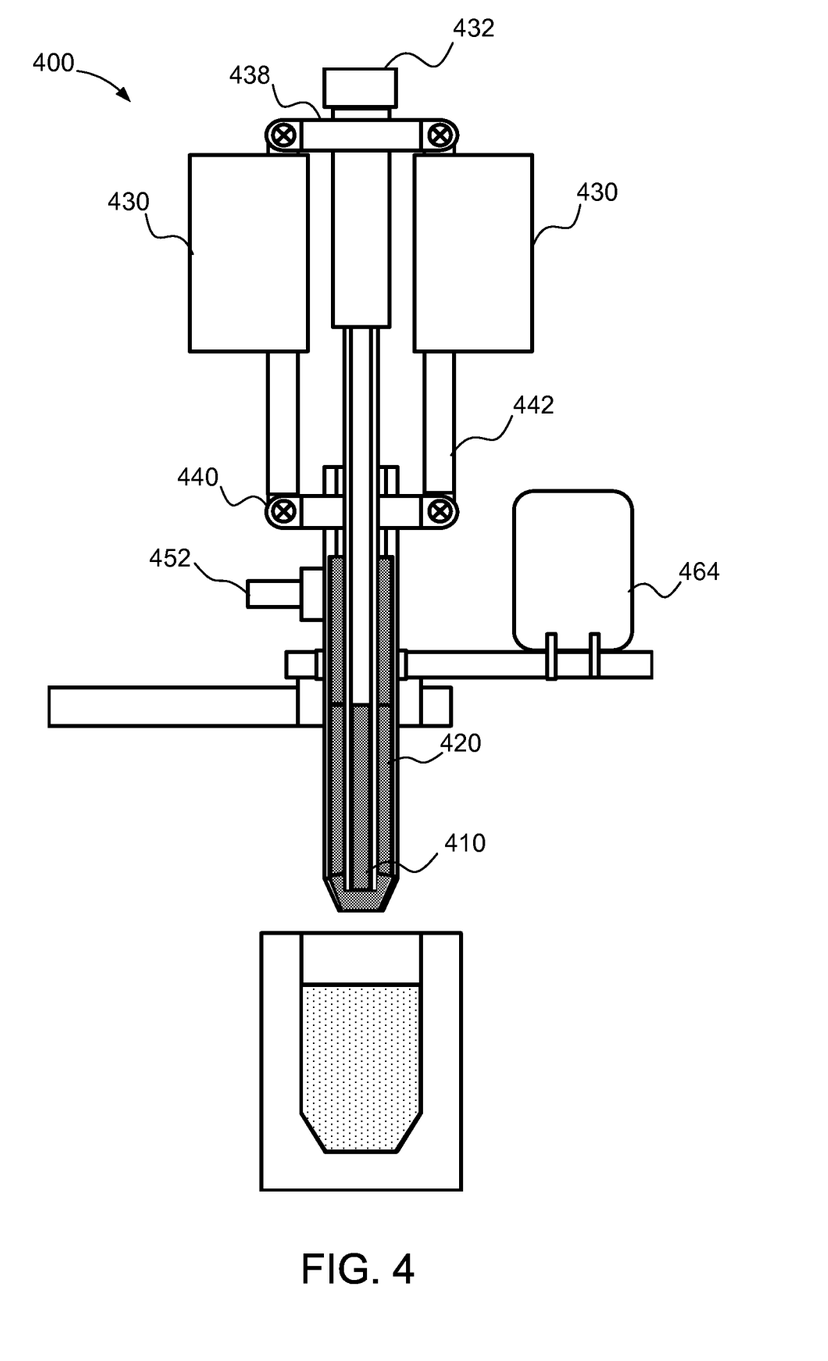
FIG. 4 illustrates an example sampling apparatus.
Figure 5:
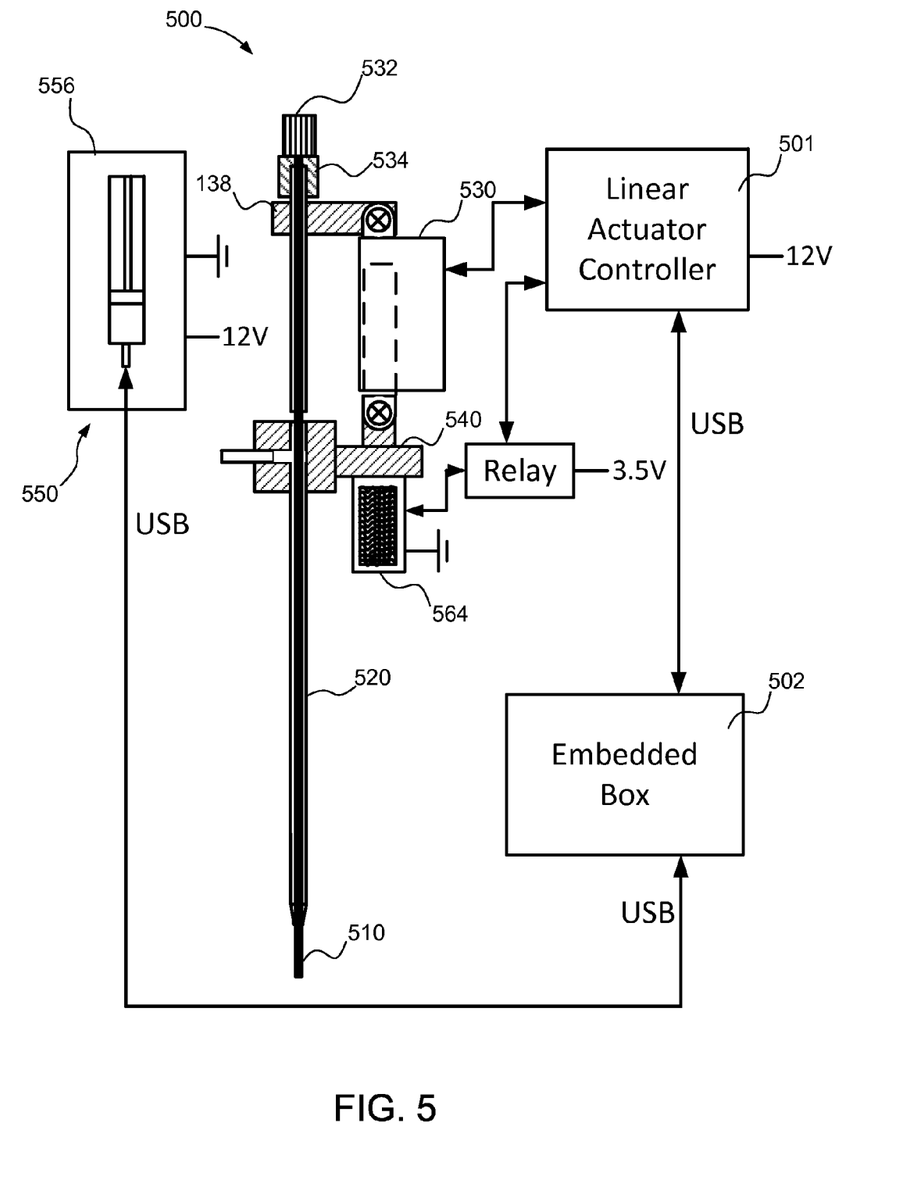
FIG. 5 illustrates an example sampling apparatus.

FIG. 4 illustrates an additional example sampling apparatus 400, utilizing two linear actuators 430 to drive movement of the chamber 420 with respect to the sampling probe 410. In this Figure, the chamber 420 is shown in an extended state, where the sampling probe 410 has drawn a volume of a marker bead solution from the chamber 420 into the probe 410. FIG. 5 illustrates an example sampling apparatus 500, which further includes computing components, such as a linear actuator controller 501. The operation and timing of the sampling apparatus 500 may be precisely controlled by software running on an embedded computer 502.

Figure 6A:
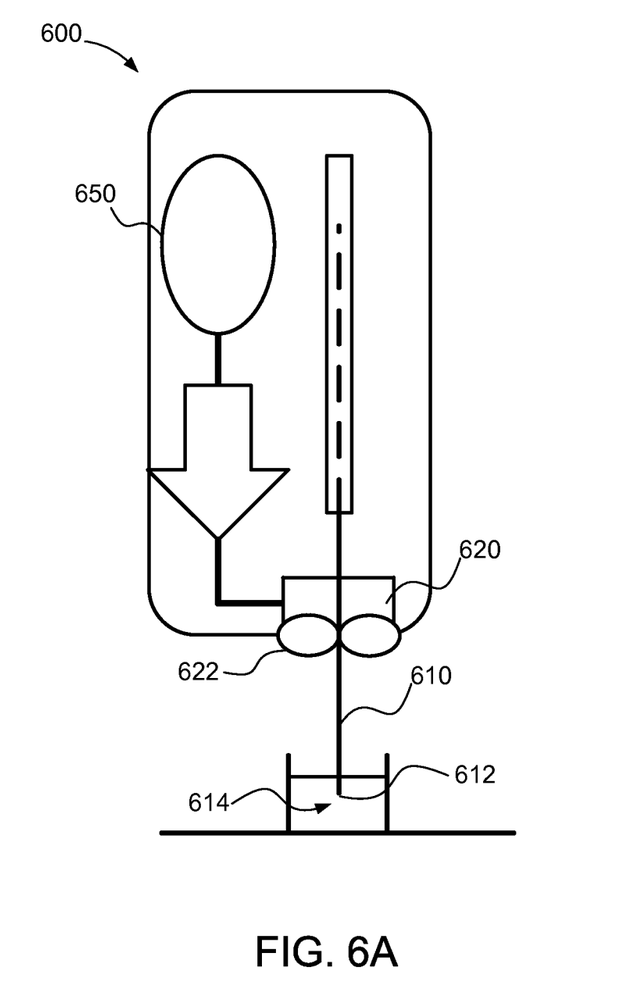
FIG. 6A illustrates an example cartridge disposed over a sample plate.
Figure 6B:
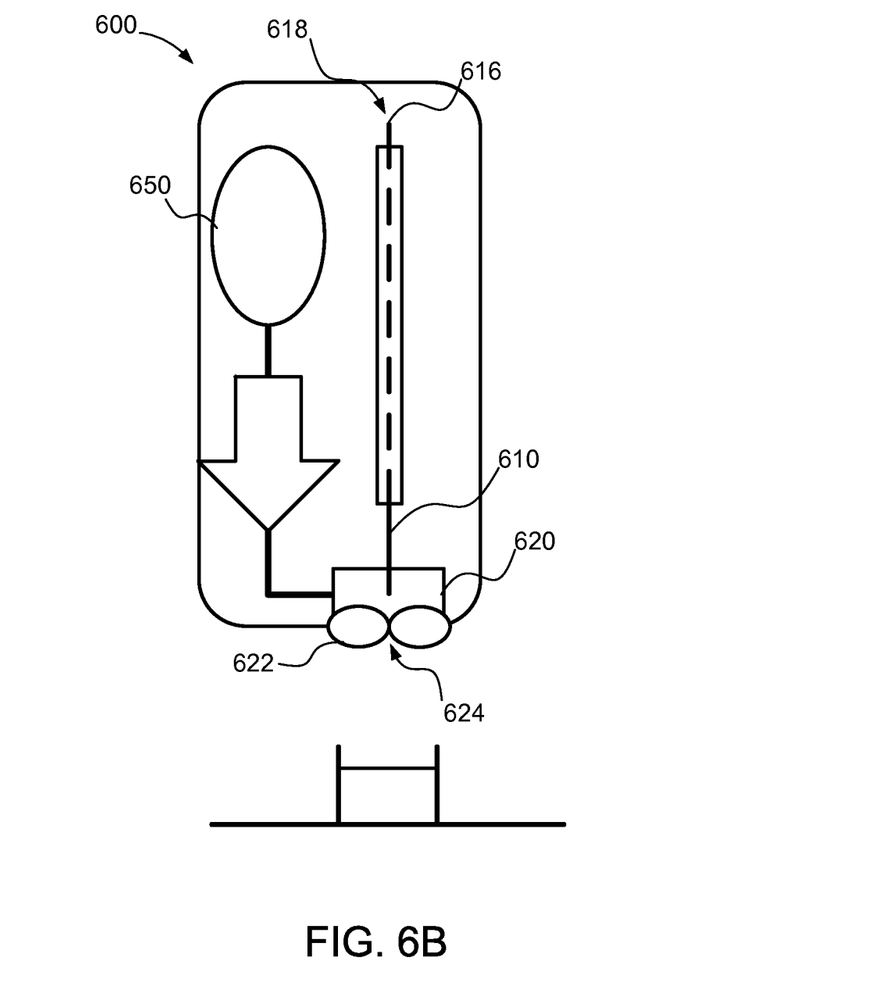
FIG. 6B illustrates a close up view of a portion of the tubing of a sampling apparatus.

FIGS. 6A and 6B illustrate a further example of a sampling apparatus 600, including a sampling probe 610 having a sampling tip 612 at a first end 614 and a flow-stream outlet 616 at a second end 618, a collar 620, and a reservoir 650 in fluid communication with the collar 620 and the sampling probe 610. Both the reservoir 650 and the collar 620 may contain a marker bead solution. The sampling probe 610 is coaxially aligned with and disposed at least partially within the collar 620. A septum 622, which may be substantially torroidal in shape, is disposed at a distal end of the collar 620 and has an opening 624 arranged co-linearly with the sampling probe 610. As used herein, with respect to torroidal configurations of a septum, "substantially" means being largely but, in some instances, not wholly that which is specified. In other words, septums may not be perfectly torroidal.

The sampling probe 610 is movable with respect to the collar 620 between a retracted position (FIG. 6B) and an extended position (FIG. 6A). In the retracted position, the sampling tip 612 of the sampling probe 610 is disposed within the collar 620. In the extended position, the sampling tip 612 of the sampling probe 610 extends through the opening 624 in the septum 622. The sampling apparatus 600 may also include an actuator (not shown) configured to move the sampling probe 610 between the retracted position and the extended position.

Similar to the embodiment of sampling apparatus 100, shown in FIG. 1, a pump (not shown), such as a peristaltic or syringe pump, may be coupled to the reservoir 650 and the collar 620 to replenish marker bead solution to the collar 620 as it is drawn out by the sampling probe 610. Further, the sampling apparatus 600 may also include a peristaltic pump in fluid communication with the flow-stream outlet of the sampling probe and a flow cytometer in fluid communication with the peristaltic pump. A vibration apparatus may be coupled to the collar to agitate the marker bead solution contained therein.

Figure 7A:
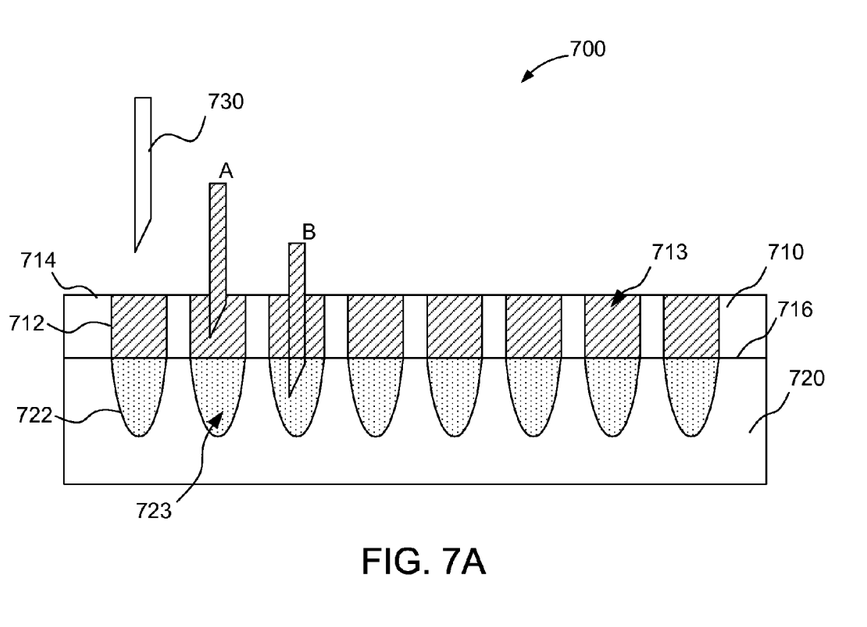
FIG. 7A illustrates an example sampling apparatus, where the probe is in an extended position.
Figure 7B:
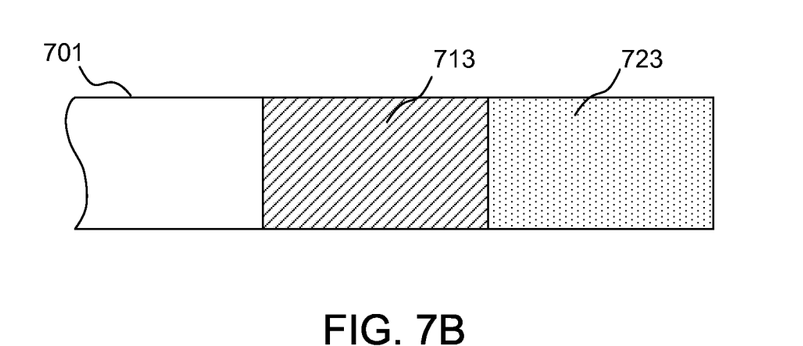
FIG. 7B illustrates the example sampling apparatus of FIG. 7A, where the probe is in an extended position.

FIGS. 7A and 7B illustrate an apparatus 700 including a cartridge 710 disposed over a sample plate 720. The cartridge 710 has at least one pierceable membrane underlying at least one chamber 712 that is configured to align with at least one sample well 722 of the sample plate 720. The at least one chamber 712 may contain a marker bead solution or a rinse solution. In the example shown in FIG. 7A, the apparatus 700 includes a first pierceable membrane 714 and a second pierceable membrane 716 that define the chamber 712 therebetween. The at least two pierceable membranes 714, 716 may be oriented substantially parallel to each other.

In some embodiments, a single chamber is provided and is arranged for alignment with each of a plurality of sample wells 722 of the sample plate 720. In other embodiments, such as that shown in FIG. 7A, a plurality of chambers 712 are provided in the cartridge and each chamber 712 is arranged for alignment with each of a plurality of sample wells 722 of the sample plate 720.

In operation, as the sample plate 720 is sampled, a probe 730 may pierce through the first membrane 714 (if present) into the bead/rinse chamber 712, aspirates some bead/rinse solution 713 (A), and then pierces through the second membrane 716 into the sample well 722 and aspirates some sample solution 723. This creates a sample pattern where each sample slug is always preceded by a bead/rinse slug (B). This bead/rinse slug demarcates the wells and also prevents the leading edge of the sample slug from contacting air.

FIG. 7B illustrates a section of tubing 701 in a flow cytometer stream, wherein volumes of sample 723 and marker bead or rinse solution 713 have been drawn in using the apparatus 700 shown in FIG. 7A.

Some functions of the example apparatuses disclosed herein include, but are not limited to: (1) Feed in marker bead fluid in between sample sips without moving the sampler to a marker bead fluid reservoir; (2) Cleaning/washing the tip of the probe that comes into contact with the sample wells in between sample sips; (3) Protect the inner probe from damage during sampler arm calibration, manual user control and calibration data errors during sampling operations; (4) Agitate marker bead fluid prior to filling the syringe pump; and (5) Dispense reagents or diluting fluid in to sample wells fluid prior to sampling.

B. Example Methods

Example methods for identifying sample boundaries of a plurality of samples are also disclosed herein. Any of the example apparatuses described above with respect to FIG. 1-FIG. 7B may be used to carry out the example methods.

In a first step of an example method, a plurality of samples comprising particles is moved into a fluid flow stream using a sampling probe. In a next step, marker beads are introduced into the fluid flow stream between adjacent samples in the plurality of samples via the sampling probe to produce a marker bead-separated plurality of samples in the fluid flow stream. The marker beads may be introduced into the fluid flow stream either by: (i) introducing the marker beads from a chamber surrounding at least a portion of the sampling probe; or (ii) introducing the marker beads from a cartridge having a pierceable membrane underlying at least one chamber containing marker beads. In a further step, the marker bead-separated plurality of samples in the fluid flow stream is guided to and through a flow cytometer. Last, the flow cytometer is operated to focus the marker bead-separated plurality of samples in the fluid flow stream and to selectively analyze the particles in each of said plurality of samples as the marker bead-separated plurality of samples in the fluid flow stream passes through the flow cytometer. The focusing can be done using any suitable technique, including but not limited to hydrodynamic focusing and acoustic focusing.

In the embodiment where the marker beads are introduced from a chamber surrounding at least a portion of the sampling probe, the step of introducing the marker beads from the chamber may include moving the sampling probe with respect to the chamber between a retracted position and an extended position. In the retracted position, a sampling tip of the sampling probe is disposed within the chamber. In the extended position, the sampling tip of the sampling probe extends through an opening in a septum disposed at a distal end of the chamber. Alternatively, marker beads from the chamber may be introduced into the fluid flow stream by moving the chamber with respect to the sampling probe between a retracted position and an extended position, where in the extended position a sampling tip of the sampling probe is contained in the chamber, and in a retracted position the sampling tip of the sampling probe extends outside of the chamber. In some examples, the method may further include vibrating the chamber to, for example, resuspend the marker beads in the solution.

In the embodiment where the marker beads may be introduced from a cartridge having a pierceable membrane underlying at least one chamber, the at least one chamber containing marker beads, the cartridge may have at least two pierceable membranes defining the at least one chamber therebetween. The chamber is arranged for alignment with at least one sample well of a sample plate. The plurality of samples comprising particles may be moved into the fluid flow stream from a plurality of respective sample wells. A first aliquot of marker beads may be introduced into the fluid flow stream prior to each of the plurality of samples and a second aliquot of marker beads is introduced into the fluid flow stream after each of the plurality of samples.

In further exemplary methods, an aliquot of a separation gas may be introduced into the fluid flow stream between adjacent samples in the plurality of samples via the sampling probe to produce a gas-separated and marker bead-separated plurality of samples in the fluid flow stream. The aliquot of the separation gas may be introduced into the fluid flow stream prior to introduction of the marker beads. Additionally or alternatively, the aliquot of the separation gas may be introduced into the fluid flow stream after introduction of the marker beads.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method for identifying sample boundaries of a plurality of samples, the method, comprising:
   (a) moving a plurality of samples comprising particles into a fluid flow stream using a sampling probe; and
   (b) introducing marker beads into the fluid flow stream between adjacent samples in the plurality of samples via the sampling probe to produce a marker bead-separated plurality of samples in the fluid flow stream, wherein the marker beads are introduced from a chamber surrounding at least a portion of the sampling probe, and wherein introducing the marker beads from the chamber comprises one of either (i) moving the sampling probe with respect to the chamber between a retracted position and an extended position, wherein a sampling tip of the sampling probe is disposed within the chamber in the retracted position and the sampling tip of the sampling probe extends through an opening in a septum disposed at a distal end of the chamber in the extended position, or (ii) moving the chamber with respect to the sampling probe between a retracted position and an extended position, wherein a sampling tip of the sampling probe is contained in the chamber in the extended position and the sampling tip of the sampling probe extends outside of the chamber in the retracted position.

2. The method of claim 1, further comprising
(c) guiding the marker bead-separated plurality of samples in the fluid flow stream to and through a flow cytometer; and
(d) operating the flow cytometer to focus the marker bead-separated plurality of samples in the fluid flow stream and to selectively analyze the particles in each of said plurality of samples as the marker bead-separated plurality of samples in the fluid flow stream passes through the flow cytometer.

3. The method of claim 1, wherein the method further comprises vibrating the chamber.

4. The method of claim 1 further comprising: introducing an aliquot of a separation gas into the fluid flow stream between adjacent samples in the plurality of samples via the sampling probe to produce a gas-separated and marker bead-separated plurality of samples in the fluid flow stream.

5. The method of claim 4, wherein the aliquot of the separation gas is introduced into the fluid flow stream prior to introduction of the marker beads.

6. The method of claim 5, wherein the aliquot of the separation gas is introduced into the fluid flow stream after introduction of the marker beads.

7. The method of claim 1, wherein the plurality of samples comprising particles are moved into the fluid flow stream from a plurality of respective sample wells.

8. The method of claim 1, wherein a first aliquot of marker beads is introduced into the fluid flow stream prior to each of the plurality of samples and a second aliquot of marker beads is introduced into the fluid flow stream after each of the plurality of samples.

9. The method of claim 1, wherein introducing the marker beads from the chamber comprises moving the sampling probe with respect to the chamber between a retracted position and an extended position, wherein a sampling tip of the sampling probe is disposed within the chamber in the retracted position and the sampling tip of the sampling probe extends through an opening in a septum disposed at a distal end of the chamber in the extended position.

10. The method of claim 9, wherein moving the sampling probe with respect to the chamber comprises actuating an actuator that is in operative communication with the sampling probe and is configured to move the sampling probe between the extended position and the retracted position.

11. The method of claim 10, wherein the sampling tip is positioned in a sample well in the extended position to thereby introduce a sample of the plurality of samples into the sampling probe, and wherein the sampling tip is positioned in the chamber in the retracted position to thereby introduce the marker beads from the chamber between adjacent samples of the plurality of samples.

12. The method of claim 11, further comprising
(c) guiding the marker bead-separated plurality of samples in the fluid flow stream to and through a flow cytometer; and
(d) operating the flow cytometer to focus the marker bead-separated plurality of samples in the fluid flow stream and to selectively analyze the particles in each of said plurality of samples as the marker bead-separated plurality of samples in the fluid flow stream passes through the flow cytometer.

13. The method of claim 9, wherein introducing the marker beads from the chamber further comprises moving the marker beads from a reservoir to the chamber, wherein the reservoir is in fluid communication with the chamber and the sampling probe.

14. The method of claim 1, wherein introducing the marker beads from the chamber comprises moving the chamber with respect to the sampling probe between a retracted position and an extended position, wherein a sampling tip of the sampling probe is contained in the chamber in the extended position and the sampling tip of the sampling probe extends outside of the chamber in the retracted position.

15. The method of claim 14, wherein the chamber has an opening at a distal end of the chamber, and wherein the sampling tip of the sampling probe extends through the opening when the chamber is in the retracted position.

16. The method of claim 15, wherein moving the chamber with respect to the sampling probe comprises actuating an actuator that is in operative communication with the chamber and is configured to move the chamber between the extended position and the retracted position.

17. The method of claim 16, wherein the sampling tip is positioned in a sample well in the retracted position to thereby introduce a sample of the plurality of samples into the sampling probe, and wherein the sampling tip is positioned in the chamber in the extended position to thereby introduce the marker beads from the chamber between adjacent samples of the plurality of samples.

18. The method of claim 17, further comprising:
(c) guiding the marker bead-separated plurality of samples in the fluid flow stream to and through a flow cytometer; and
(d) operating the flow cytometer to focus the marker bead-separated plurality of samples in the fluid flow stream and to selectively analyze the particles in each of said plurality of samples as the marker bead-separated plurality of samples in the fluid flow stream passes through the flow cytometer.

19. The method of claim 18, wherein moving the plurality of samples comprising particles into the fluid flow stream comprises activating a peristaltic pump in fluid communication with the fluid flow stream.

20. The method of claim 14, wherein introducing the marker beads from the chamber further comprises moving the marker beads from a reservoir to the chamber, wherein the reservoir is in fluid communication with the chamber and the sampling probe.

* * * * *